United States Patent [19]

Misra

[11] Patent Number: 5,332,822
[45] Date of Patent: Jul. 26, 1994

[54] HETEROAROMATIC AND THIOHETEROAROMATIC SUBSTITUTED SULFONAMIDE THROMBIN INHIBITORS

[75] Inventor: Raj N. Misra, Hopewell, N.J.

[73] Assignee: Bristol-Myers Squibb Company, Princeton, N.J.

[21] Appl. No.: 996,755

[22] Filed: Dec. 24, 1992

[51] Int. Cl.$^5$ .................. C07D 215/36; C07D 215/58; C07D 215/02

[52] U.S. Cl. .................. 546/164; 540/467; 540/470; 540/450; 540/544; 540/553; 540/575; 544/3; 544/53; 544/88; 544/98; 544/238; 544/242; 546/166; 546/256; 546/275; 548/146; 548/206; 548/215; 548/364.1; 548/311.1; 548/517

[58] Field of Search .............. 546/164, 166, 256, 275; 540/467, 470, 450, 544, 553, 575; 544/53, 3, 88, 98, 238, 242; 548/146, 206, 215, 364.1, 311.1, 517; 514/183, 211, 212, 226.8, 228.8, 256, 248, 314, 340, 365, 372, 374, 378, 385, 407

[56] References Cited

U.S. PATENT DOCUMENTS

| | | | |
|---|---|---|---|
| 4,055,651 | 10/1977 | Okamoto et al. | 424/267 |
| 4,066,758 | 1/1978 | Okamoto et al. | 424/244 |
| 4,066,773 | 1/1978 | Okamoto et al. | 424/267 |
| 4,069,323 | 1/1978 | Okamoto et al. | 424/244 |
| 4,073,914 | 2/1978 | Kikumoto et al. | 424/267 |
| 4,117,127 | 9/1978 | Okamoto et al. | 424/247 |
| 4,201,863 | 5/1980 | Okamoto et al. | 546/166 |
| 4,258,192 | 3/1981 | Okamoto et al. | 546/166 |
| 4,764,618 | 8/1988 | Kikumoto et al. | 546/196 |

OTHER PUBLICATIONS

J. Indian Chem. Soc., 53(3), pp. 274–278, Mar. 1976.
CA 62:2434f, "Screening of Antipolio . . . " by Otaki et al., 1965.
Merck Index, 9th Edition, #7770, p. 7767, 1976.
Angliker, Herbert et al., "Pseudoarginine: synthesis and properties of derivatives of δ-(1-imidazolyl)norvaline", Biochem. J. (1990) 266, 829–834.
Hijikata-Okunomiya, Akiko et al., "A Strategy for a Rational Approach to Designing Synthetic Selective Inhibitors", Seminars in Thrombosis and Hemostasis-vol. 18, No. 1, 1992, pp. 135–149.

Primary Examiner—C. Warren Ivy
Assistant Examiner—D. Margaret M. Mach
Attorney, Agent, or Firm—Burton Rodney

[57] ABSTRACT

Sulfonamide thrombin inhibitors are provided which have the structure

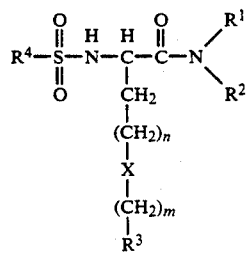

including all stereoisomers thereof, wherein X is S or —CH$_2$—; m is 0, 1 or 2 when X is —S— or m is 0 when X is —CH$_2$—; n is 1, 2 or 3; R$^1$ and R$^2$ are independently H, lower alkyl, cyclo-alkyl, aryl, heteroaryl or heteroarylalkyl, or R$^1$ and R$^2$ can be taken together with the N atom to which they are attached to form a 5- to 8-membered ring which may optionally contain an additional N, O or S atom in the ring; R$^3$ is heteroaryl; and R$^4$ is alkyl, cycloalkyl, aryl, heteroaryl, quinolinyl or tetrahydroquinolinyl, and pharmaceutically acceptable salts thereof.

15 Claims, No Drawings

HETEROAROMATIC AND THIOHETEROAROMATIC SUBSTITUTED SULFONAMIDE THROMBIN INHIBITORS

FIELD OF INVENTION

The present invention relates to heteroaryl or thioheteroaryl substituted sulfonamides, such as pyridine-, thioimidazole-, or thiopyridinenaphthalenesulfonamides, which are thrombin inhibitors and thus inhibit formation of thrombi.

DESCRIPTION OF THE INVENTION

In accordance with the present invention compounds are provided which are thrombin inhibitors which have the structure I

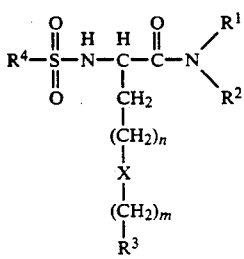

including all stereoisomers thereof,
wherein
X is —S— or —CH$_2$—;
m is 0, 1 or 2 when X is S or m is 0 when X is CH$_2$—;
n is 1, 2 or 3;
R$^1$ and R$^2$ may be the same or different and are independently hydrogen, lower alkyl, cycloalkyl, aryl, heteroaryl, or heteroarylalkyl, or R$^1$ and R$^2$ can be taken together with the nitrogen atom to which they attached to form a 5-to 8- membered N-containing heterocyclic ring, which may optionally contain an additional N, O or S atom in the ring, which may be unsubstituted or substituted on a carbon atom or on a nitrogen atom with lower alkyl, carboxy, amido, carboalkoxy, aryl, cycloalkyl, hydroxy, alkoxy, amino, alkylamino or dialkylamino;
R$^3$ is heteroaryl; and
R$^4$ is alkyl, cycloalkyl, aryl, tetrahydronaphthyl, heteroaryl, quinolinyl, or tetrahydroquinolinyl;
including
pharmaceutically acceptable salts thereof.

Accordingly, the compounds of the invention may have the following structures:

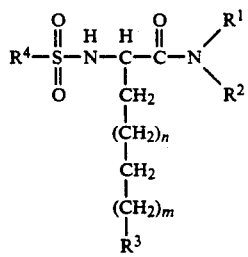

IA

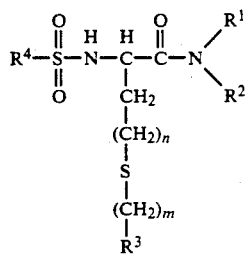

IB

The term "lower alkyl" or "alkyl" as employed herein by itself or as part of another group includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents, an aryl substituent, an alkylaryl substituent, a haloaryl substituent, a cycloalkyl substituent, an alkylcycloalkyl substituent, an alkenyl substituent, an alkynyl substituent, an alkoxy substituent, hydroxy and/or a carboxy substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy and/or hydroxy group.

The term "aryl" or "Ar" as employed herein by itself or as part of another group refers to monocyclic or bicyclic aromatic groups containing phenyl, naphthyl, or tetrahydronaphthyl. Aryl (or Ar), phenyl or naphthyl may include substituted aryl, substituted phenyl or substituted naphthyl, which may include 1 or 2 substituents on either the phenyl or naphthyl such as lower alkyl, cyano, amino, alkylamino, dialkylamino, nitro, carboxy, carboalkoxy, trifluoromethyl, halogen (Cl, Br, I or F), lower alkoxy, arylalkoxy, hydroxy, alkylthio, alkylsulfinyl, alkysulfonyl, arylthio, arylsulfinyl and/or arylsulfonyl.

The term "aralkyl", "aryl-alkyl" or "aryl-lower alkyl" as used herein by itself or as part of another group refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein by itself or as part of another group refers to chlorine, bromine, fluorine or iodine with chlorine being preferred.

The term "lower alkenyl" or "alkenyl" by itself or as part of another group as employed herein includes a carbon chain by itself or as part of another group of up to 16 carbons, preferably 3 to 10 carbons, containing one double bond such as 2-propenyl, 2-butenyl, 3-butenyl, 2-pentenyl, 4-pentenyl and the like, and may include a halogen substituent such as I, Cl, or F.

The term "lower alkynyl" or "alkynyl" by itself or as part of another group as employed herein includes a carbon chain of up to 16 carbons, preferably 3 to 10 carbons, containing one triple bond such as 2-propynyl, 2-butynyl, 3-butynyl and the like.

The term "heteroaryl" or "heteroaromatic" by itself or as part of another group refers to a 5-to 10- membered monocyclic or bicyclic aromatic ring which includes 1 or 2 hetero atoms such as nitrogen, oxygen or sulfur, which as an R¹ or R² substituent is not directly linked through a hetero atom to the "N" of the

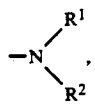

such as

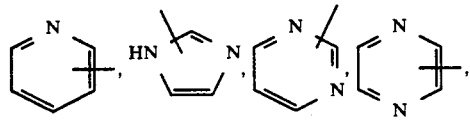

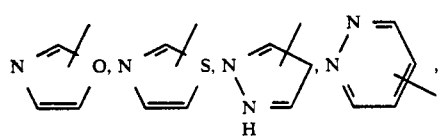

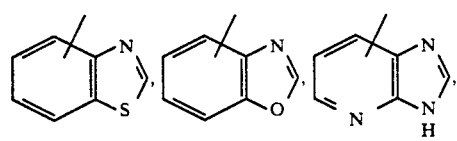

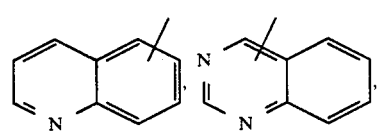

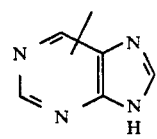

and the like.

The heteroaryl rings may optionally include 1 or 2 substituents such as halogen (Cl, Br, F or CF₃), lower alkyl, lower alkoxy, cyano, hydroxy, carboxy, amido, carboalkoxy, aryl, cycloalkyl, alkoxy, alkylthio, alkylsulfinyl, alkylsulfonyl, arylthio, arylsulfinyl, arylsulfonyl, amino, lower alkylamino and/or di-lower alkylamino, which substituents may be linked to a carbon atom or nitrogen atom.

Preferred are compounds of formula I wherein R⁴ is aryl, preferably 2-naphthyl, 7-methoxy-2-naphthyl or tetrahydroquinoline, n is 2, m is 0, X is S, R³ is imidazolyl which may be unsubstituted or substituted with alkyl, and R¹ and R² are taken together to form a 5 to 7 membered heterocyclic ring which preferably is piperidinyl such as alkyl-substituted piperidinyl, most preferably 4-methyl piperidinyl.

Preferred are compounds of the invention having the structure IA¹ in which the stereo-chemistry of the α-carbon is S.

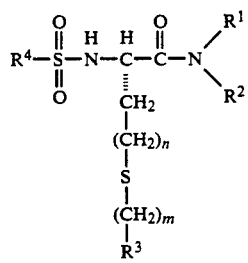

The compounds of formula I of the invention may be prepared as outlined below.

Compounds of the invention I where X is S or CH₂ may be prepared starting with amide II

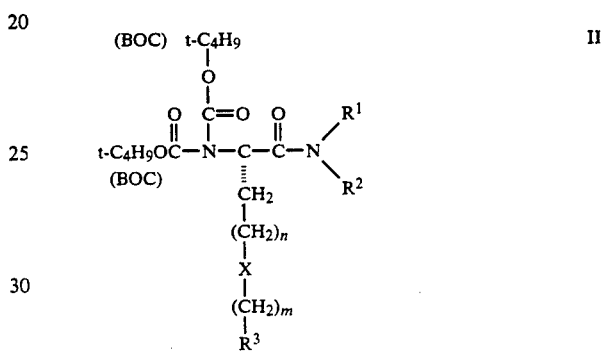

which is made to undergo a deprotecting reaction wherein II is treated with hydrogen chloride in the presence of dioxane or trifluoroacetic acid in dichloromethane to form III.

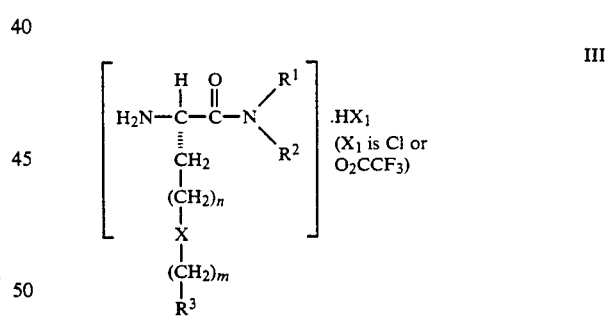

Amine salt III is then treated with sulfonyl chloride IV

in the presence of an organic base such as triethylamine or diisopropylethylamine, and an inert organic solvent such as dichloromethane, chloroform or THF, under an inert atmosphere such as argon at a reduced temperature of from about −20° to about 15° C., to form the sulfonamide I of the invention.

The amide II where X is S may be prepared starting with acid A where n is 1, 2 or 3, according to the following reaction sequence.

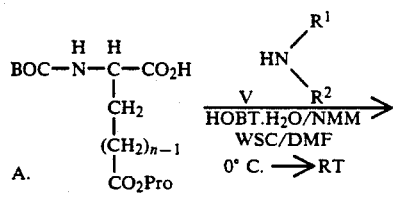
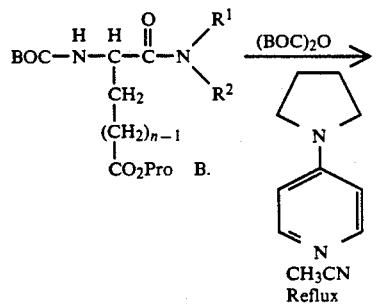
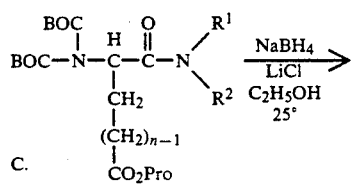
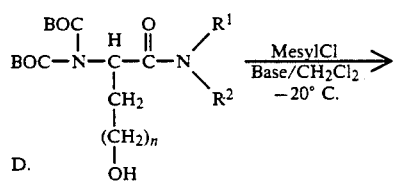
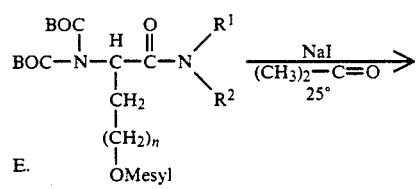
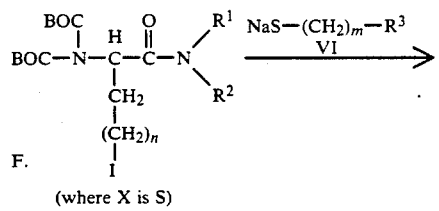
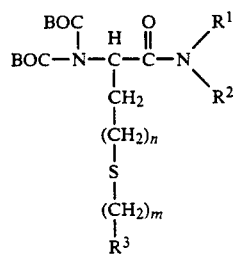

Amide II
(where X is S,
that is IIA)

As seen in the above reaction sequence, protected amino acid A

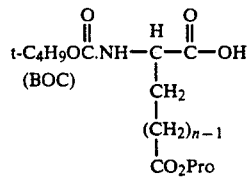

wherein Pro is methyl, ethyl or benzyl, is made to undergo a carbodiimide coupling reaction with the amine V

in the presence of ethyl 3-(3-dimethylamino)propylcarbodiimidehydrochoride (WSC) or dicyclohexylcarbodiimide (DCC), and 1-hydroxybenzotriazole monohydrate (HOBT), and N-methylmorpholine or triethylamine, and an inert organic solvent such as dimethylformamide (DMF), or tetrahydrofuran (THF), under an inert atmosphere such as argon, to form amide B.

Amide B is treated with (BOC)₂O, and 4-pyrrolidinopyridine or 4-dimethylaminopyridine in the presence of acetonitrile to form amide C. Amide C is then reduced by treating C with a reducing agent such as diisobutylaluminum hydride (DIBAL) in the presence of methylene chloride or sodium borohydride in the presence of lithium chloride and ethanol to form alcohol D. Alcohol D is made to undergo iodide formation by treating a solution of alcohol D with mesyl chloride in the presence of organic base such as triethylamine or diisopropylethylamine, to form mesylate E which is treated with sodium iodide in acetone solution to form iodide F.

Iodide F is then treated with a solution of the sodium anion VI

in dry inert organic solvent such as dry tetrahydrofuran or dimethylformamide (DMF), under an inert atmosphere such as argon, to form amide IIA as described above.

Alternatively, compounds of Formula I where X is S may be prepared starting with alcohol

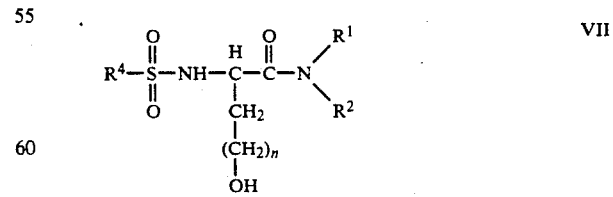

which is made to undergo iodide formation by treating a solution of alcohol VII with mesylchloride in the presence of organic base such as triethylamine or diisopropylethylamine and then with sodium iodide in the presence of acetone to form iodide VIII.

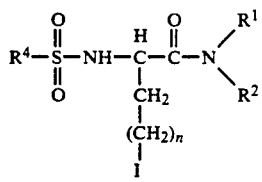

VIII

Iodide VIII is then treated with a solution of thiol [R³(CH₂)ₘSH] in a dry inert organic solvent such as DMF or DMSO, under an inert atmosphere such as argon, at a temperature of from about 25° to about 100° C., to form the formula I compound where X is S of the invention.

The starting alcohol VII may be prepared as follows.

Amide B is made to undergo a deprotecting reaction wherein amide B is treated with trifluoroacetic acid in dichloromethane or hydrogen chloride in dioxane, under an inert atmosphere such as argon, at reduced temperature of from about 0° to about 25° C., to form amide XI.

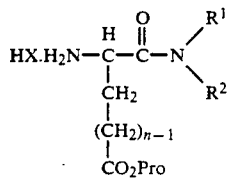

XI

Amide XI is then made to undergo sulfonamide formation by treating XI in the presence of an inert organic solvent such as dichloromethane, chloroform or tetrahydrofuran, under an inert atmosphere such as argon at a reduced temperature of from about −20° to about 15° C., with a sulfonyl chloride of the structure IV

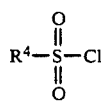

IV and organic base such as triethylamine or diisopropylethylamine, to form sulfonamide XII.

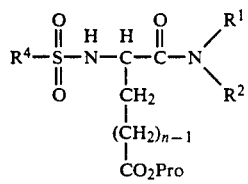

XII

Sulfonamide XII is then reduced by treatment of XII with diisobutylaluminum hydride (DIBAL-H) in the presence of an inert organic solvent such as THF or methylene chloride or toluene or with sodium borohydride, in the presence of lithium chloride and ethanol, under an inert atmosphere such as argon to form alcohol VII.

The amide II where X is CH₂ may be prepared starting with alcohol D where n is 1, 2 or 3, according to the following reaction sequence.

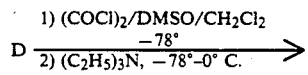

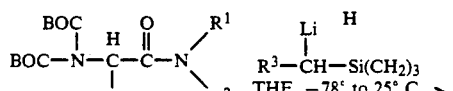

G

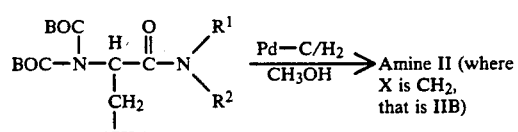

J

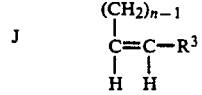

IIB $$\begin{bmatrix} & H & O & R^1 \\ H_2N-C-C-N & \\ & CH_2 & R^2 \\ & (CH_2)_n \\ & CH_2 \\ & R^3 \end{bmatrix} \cdot HCl$$

IIIA

As seen in the above reaction sequence, alcohol D is subjected to a Swern oxidation wherein alcohol D is treated with a mixture of oxalyl chloride and dimethylsulfoxide in methylene chloride at a reduced temperature of within the range of from about −78° to about −20° C. The reaction mixture is treated with organic base such as triethylamine or diisopropylethylamine and warmed to a temperature of within the range of from about 0° to about 25° C. Aldehyde G is formed which is made to undergo a Petersen olefination reaction wherein G is treated with lithiosilane H $$\text{H} \quad R^3-\overset{\overset{\text{Li}}{|}}{\text{CH}}-\text{Si}(CH_2)_3$$

at a reduced temperature of within the range of from about −78° to about 25° C., in the presence of an inert organic solvent such as tetrahydrofuran to form olefin J. Olefin J is reduced by reaction with H₂ in the presence of a catalyst such as palladium on activated carbon in the presence of methanol or other alcohol solvent to form amide II where X is CH₂, that is IIB. Amide IIB is then deprotected as described hereinbefore with respect to amide II to form amine salt IIIA which may be used in place of amine salt III to form sulfonamide I as described hereinbefore.

The compounds of formula I of the invention can be obtained as pharmaceutically acceptable acid addition salts by reacting a free base with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting a free carboxylic acid with a base, such as sodium hydroxide, potassium hydroxide, ammonium hydroxide, triethylamine, procaine, dibenzylamine, 1-ephenamine, N,N'-dibenzylethylenediamine, N-ethylpiperidine, arginine, lysine or the like.

The compounds of the present invention are serine protease inhibitors, and in particular inhibit thrombin, Factor Xa, and/or trypsin. The compounds of the present invention are useful for the treatment or prophylaxis of those processes which involve the production and/or action of thrombin. This includes a number of thrombotic and prothrombotic states in which the coagulation cascade is activated which include, but are not limited to, deep vein thrombosis (DVT), consumptive hemorrhagic disorders (such as disseminated intravascular coagulopathy (DIC), renal allograft rejection and hemolytic uremic syndrome, Kasabach-Merritt syndrome, pulmonary embolism, myocardial infarction, stroke, thromboembolic complications of surgery (such as coronary artery bypass graft, hip replacement and endarterectomy) and peripheral arterial occlusion. In addition to its effects on the coagulation process, thrombin has been shown to activate a large number of cells (such as neutrophils, fibroblasts, endothelial cells, and smooth muscle cells). Therefore, the compounds of the present invention may also be useful for the treatment or prophylaxis of adult respiratory distress syndrome, septic shock, septicemia, inflammatory responses which include, but are not limited to, edema, acute or chronic atherosclerosis, and reperfusion damage.

The compounds of the invention may also be useful in treating neoplasia/metastasis (in particular those which utilize fibrin) and neurodengenerative diseases such as Alzheimer's disease and Parkinson's disease. In addition, the compounds of the present invention may be useful to prevent restenosis following arterial injury induced by endogenous (rupture of an atherosclerotic plaque) or exogenous (invasive cardiological procedure) events.

The compounds of the present invention may also be used as an anticoagulant in extracorporeal blood circuits, such as those necessary in dialysis and surgery (such as coronary artery bypass surgery).

The compounds of the present invention may also be used in combination with thrombolytic agents, such as tissue plasminogen activator (natural or recombinant), streptokinase, urokinase, prourokinase, anisolated stretokinase plasminogen activator complex (ASPAC), animal salivary gland plasminogen activators, and the like. The compounds of the present invention may act in a synergistic fashion to prevent reocclusion following a successful thrombolytic therapy and/or reduce the time to reperfusion. The compounds of the present invention may also allow for reduced doses of the thrombolytic agent to be used and therefore minimize potential hemmorhagic side-effects. The compounds of the present invention may also prevent acute long-term reocclusion and/or restenosis following arterial recanalization procedures, including, but not limited to, balloon angioplasty, placement of arterial stents, and laser and/or mechanical atherectomy procedures.

The compounds of the present invention may also be used in combination with other antithrombotic or anticoagulant drugs such as thromboxane receptor antagonists, prostacyclin mimetics, phosphodiesterase inhibitors, fibrinogen antagonists, and the like.

Compounds of the present invention that inhibit trypsin may also be useful for the treatment of pancreatitis.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses, for a period necessary to alleviate the condition requiring treatment in accordance with the invention.

The active substance can be utilized in a composition such as tablet, capsule, solution or suspension containing about 5 to about 500 mg per unit of dosage of a compound or mixture of compounds of formula I. The compounds of the invention may be compounded in conventional manner with a physiologically acceptable vehicle or carrier, excipient, binder, preservative, stabilizer, flavor, etc., as called for by accepted pharmaceutical practice.

The following Examples represent preferred embodiments of the present invention. Unless otherwise indicated, all temperatures are expressed in degrees Centigrade.

EXAMPLE 1

(S)-N-[4-[(1-Methyl-1H-imidazol-2-yl)thio]-1-[(4-methyl-1-piperidinyl)carbonyl]butyl]-2-naphthalenesulfonamide

A.

(S)-$\beta$-[[(1,1-Dimethylethoxy)carbonyl]-amino]-4-methyl-$\alpha$-oxo-1-piperidinepentanoic acid, phenylmethyl ester To a clear solution of 8.00 g (23.7 mmol, Bachem) of N-Boc-L-glutamic acid-$\gamma$-benzyl ester, in 150 mL of DMF was added 3.1 mL (26 mmol, Aldrich) of 4-methylpiperidine and 4.0 g (26 mmol, Schweizerhall) of 1-hydroxybenzotriazole monohydrate. The mixture was cooled to 0° C. and treated with 5.2 mL (47 mmol, Aldrich), of N-methylmorpholine, followed by the addition of 5.0 g (26 mmol, Bachem) of WSC. The mixture was stirred at 0° C. for 2 hours and at room temperature for 4 hours. The mixture was concentrated in high vacuum. The residue was worked up with 300 mL of EtOAc, washed with 200 mL of 1N HCl and 200 mL of a saturated aqueous solution of NaHCO$_3$, H$_2$O and brine; dried (MgSO$_4$) and concentrated in vacuo to afford 9.92 g (23.7 mmol, 100%) of title compound as a clear oil.

B.

(S)-$\beta$-[Bis[(1,1-dimethylethoxy)carbonyl]-4-methyl-$\alpha$-oxo-1-piperidinepentanoic acid, phenylmethyl ester To a syrup of 6.50 g (15.5 mmol) of Part A compound in 1.0 mL of acetonitrile was added 1.38 g (9.3 mmol, Aldrich) of 4-pyrrolidinopyridine and treated with 43.4 g (199 mmol, Fluka) of di-tert-butyl dicarbonate dropwise over a period of 6 hours at 87° C. The resulting black light oil was purified by flash chromatography (280 g, Merck silica gel, 15% EtOAc/hexane) to afford pure 4.7 g (9.0 mmol, 60%) of title compound as a clear oil.

C.
(S)-[4-Hydroxy-1-[(4-methyl-1-piperidinyl)carbonyl]-butyl]imidodicarbonic acid, bis(1,1-dimethylethyl) ester A light yellow solution of 4.4 g (8.5 mmol of Part B compound in 50 mL (Aldrich) anhydrous EtOH was treated with 1.44 g (34 mmol, Aldrich) of lithium chloride. The slurry was allowed to stir at room temperature for 15 minutes until the solid was completely dissolved. The yellow solution was treated with 624 mg (17 mmol, Aldrich) of sodium borohydride. The mixture was stirred at room temperature for 26 hours. The mixture was treated then with a second portion of 1.44 g (34 mmol, Aldrich) of lithium chloride and 642 mg (17 mmol, Aldrich) of sodium borohydride. After stirred at room temperature 24 hours, the mixture was treated with a third portion of 1.44 g (34 mmol, Aldrich) of lithium chloride and 642 mg (17 mmol, Aldrich) of sodium borohydride and allowed to stir for 24 hours. The crude reaction mixture was quenched with 10 mL of $H_2O$. The mixture was concentrated in vacuo. The residue was partitioned between 100 mL of 0.5N HCl and 200 mL of EtOAc. The organic layer was separated and washed with 100 mL of a saturated aqueous solution of $NaHCO_3$ and brine; dried ($MgSO_4$) and concentrated in vacuo. The residue was purified by flash chromatography (100 g, Merck silica gel, 40% EtOAc/hexane) to afford 2.5 g (6.0 mmol, 71%) of pure title compound as a clear oil.

D.
(S)-[1-[(4-Methyl-1-piperidinyl)carbonyl]-4-[(methylsulfonyl)oxy]butyl]imidodicarbonic acid, bis(1,1-dimethylethyl) ester A clear solution of 2.5 g (6.0 mmol) of Part C compound in 10 mL of $CH_2Cl_2$ (distilled from $P_2O_5$) was cooled to −20° C. and treated with 1.3 mL (9.0 mmol) of triethylamine ($Et_3N$) (distilled from $CaH_2$), followed by the addition of 0.60mL (7.3 mmol, Aldrich) of methanesulfonyl chloride. The mixture was stirred at −20° C. for 1 hour. The crude mixture was diluted with 20 mL of $CH_2Cl_2$, washed with 20 mL of 1N HCl and 20 mL of a saturated aqueous solution of $NaHCO_3$ and brine; dried ($MgSO_4$), and concentrated in vacuo to afford 2.9 g (5.9 mmol, 97%) of title compound.

E.
(S)-[4-Iodo-1-[(4-methylpiperidinyl)carbonyl]butyl]imidodicarbonic acid, bis-(1,1-dimethylethyl) ester To the light yellow solution of 2.8 g (5.6 mmol) of Part D compound in 60 mL fresh acetone (Burdick and Jackson) was added 4.2 g (28 mmol) of sodium iodide. The mixture was stirred in the dark at room temperature for 16 hours. The crude reaction mixture was concentrated in vacuo. The residue was diluted with EtOAc, washed with 200 mL aqueous 5% sodium thiosulfate and an aqueous solution of saturated $NaHCO_3$ and brine; dried ($MgSO_4$) and concentrated in vacuo to give 2.73 g (5.20 mmol, 93%) of title compound.

F.
(S)-[4-[(1-Methyl-1H-imidazol-2-yl)thio]-1-[(4-methyl-1-piperidinyl)carbonyl]butyl]-imidodicarbonic acid, bis(1,1-dimethylethyl) ester The oil was removed from 76 mg (60% in oil, 1.9 mmol, Aldrich) of sodium hydride dispersion by three washes with hexane then 2 mL of sieve-dried DMF were added. The slurry was cooled in an ice-bath then added in one portion was 216 mg (1.89 mmol) of 2-mercapto-1-methyl-imidazole (Pfaltz and Bauer). The reaction mixture was stirred for 15 minutes to give a clear solution then a solution of 996 mg (1.90 mmol) of Part E iodide in 2 mL of DMF was added dropwise. The reaction mixture was stirred for 30 minutes then partitioned between 30 mL of water and 30 mL of ethyl acetate. The organic layer was separated, washed with two-30 mL portions of water, dried (sodium sulfate) and concentrated in vacuo to an oil. The crude oil was purified by flash chromatography (Merck silica, 15×3.0 cm, ethyl acetate) to afford 880 mg (1.73 mmol, 91%) of title compound as a colorless oil.

G.
(S)-2-Amino-5-[(1-methyl-1H-imidazol-2-yl)thio]-1-[(methyl-1-piperidinyl)carbonyl]-1-pentanone, dihydrochloride To a solution of 814 mg (1.60 mmol) of Part F compound in 1 mL of dioxane (Burdick and Jackson) was added at room temperature 4.0 mL (4M in dioxane, 16 mmol, Aldrich) of HCl solution. The reaction mixture was stirred for 18 hours then concentrated in vacuo to give an oil. The crude oil was solubilized in 5 mL of methanol and then concentrated in vacuo; repeated a second time to afford 605 mg (1.58 mmol, 99%) of title compound as a solid white foam.

H.
(S)-N-[4-[(1-Methyl-1H-imidazol-2-yl)thio]-1-[(4-methyl-1-piperidinyl)carbonyl]butyl]-2-naphthalenesulfonamide To a solution of 200 mg (0.52 mmol) of Part G amine hydrochloride and 0.30 mL (2.1 mmol, distilled from calcium hydride) of triethylamine in 3 mL of methylene chloride (distilled from phosphorous pentoxide) cooled at 0° was added 117 mg (0.52 mmol, Aldrich) of 2-naphthalenesulfonyl chloride in one portion. The reaction mixture was stirred for 15 minutes then partitioned between 20 mL of ethyl acetate and 20 mL of saturated aqueous sodium bicarbonate solution. The organic layer was separated, dried (sodium sulfate) and concentrated in vacuo to give an oil. The crude material was purified by flash chromatography (Merck silica, 12×3.0 cm, 1:50 methanol/ethyl acetate) to give an oil which was crystallized (ethyl acetate/hexane) to afford 210 mg (0.42 mmol, 81%) of (S)-N-[4-[(1-methyl-1H-imidazol-2-yl)thio]-1-[(4-methyl-1 piperidinyl)carbonyl]butyl]-2-naphthalenesulfonamide as white crystals, mp 122–124.

Analysis calcd for $C_{25}H_{32}N_4O_3S_2$:
C, 59.97; H, 6.44; N, 11.19; S, 12.81.
Found: C, 60.02; H, 6.46; N, 11.18; S, 12.64.

EXAMPLE 2

(S)-5-(Dimethylamino)-N-[4-[(1-methyl-1H-imidazol-2-yl)thio]-1-[(4-methyl-1-piperidinyl)carbonyl]butyl]-1-naphthalenesulfonamide To a solution of 200 mg (0.52 mmol) of Example 1, Part G amine hydrochloride and 0.30 mL (2.1 mmol, distilled from calcium hydride) of triethylamine in 3 mL of methylene chloride (distilled from phosphorous pentoxide) cooled to 0° was added 140 mg (0.52 mmol, Aldrich) of dansyl chloride in one portion. The reaction mixture was stirred for 30 minutes then partitioned between 30 mL of ethyl acetate and 30 mL of water. The organic layer was separated, dried (sodium sulfate) and concentrated in vacuo to give a yellow-green oil. The crude material was purified by flash chromatography (Merck silica, 12×3.0 cm, 3:97 methanol/ethyl acetate) to afford 235 mg (0.43 mmol, 83%)of the (S)-5-(dimethylamino)-N-[4-[(1-methyl-1H-imidazol-2-yl)thio]-1-[(4-methyl-1-piperidinyl)carbonyl]butyl]-1-naphthalenesulfonamide as a pale green solid foam.

Analysis calcd for $C_{27}H_{37}N_5O_3S_2$:
C, 59.64; H, 6.86; N, 12.88; S, 11.79.
Found: C, 59.47; H, 6.89; N, 12.76; S, 11.46.

EXAMPLE 3

A.

(S)-N-[4-[(1H-Imidazol-2-yl)thio]-1-[(4-methyl-1-piperidinyl)carbonyl]butyl]-2-naphthalenesulfonamide

A.

(S)-[4-(1H-Imidazol-2-ylthio)-1-[(4-methyl-1-piperidinyl)carbonyl]butyl]imidodicarbonic acid, bis(1,1-dimethylethyl) ester The oil was removed from 67 mg (60% in oil, 1.7 mmol, Aldrich) of sodium hydride dispersion by three washes with hexane then added was 2 mL of sieve-dried DMF. The slurry was cooled in an ice-bath then added in one portion was 167 mg (1.67 mmol) of 2-mercaptoimidazole (Aldrich). The reaction mixture was stirred for 20 minutes to give a clear solution then a solution of 925 mg (1.77 mmol) of Example 1, Part E iodide in 3 mL of DMF was added dropwise. The reaction mixture was stirred for 30 minutes then partitioned between 30 mL of 1M aqueous organic layer was separated, washed with two-30 mL portions of water, dried (sodium sulfate) and concentrated in vacuo to an oil. The crude oil was purified by flash chromatography (Merck silica, 14×3.0 cm, ethyl acetate) to afford 760 mg (1.53 mmol, 92%)of (S)-N-[4-[(1H-imidazol-2-yl)thio]-1-[(4-methyl-1-piperidinyl)carbonyl]butyl]-2-naphthalenesulfonamide as a colorless glass.

B.

(S)-2-Amino-5-(1H-imidazol-2-ylthio)-1-[(4-methyl-1-piperidinyl)carbonyl]-1-pentanone, dihydrochloride To a solution of 730 mg (1.47 mmol) of Part A compound in 1 mL of dioxane (Burdick and Jackson) cooled in an ambient water bath was added 4.0 mL (4M in dioxane, 16 mmol, Aldrich) of HCl solution. The reaction mixture was stirred for 5 hours then concentrated in vacuo to give an oil. The crude oil was solubilized in 5 mL of methanol and then concentrated in vacuo; repeated a second time to afford 540 mg (1.46 mmol, 100%) of title compound as a hygroscopic pale yellow foam.

C.

(S)-N-[4-[(1H-imidazol-2-yl)thio]-1-[(4-methyl-1-piperidinyl)carbonyl]butyl]-2-naphthalenesulfonamide To a solution of 200 mg (0.54 mmol) of Part B amine hydrochloride and 0.30 mL (2.1 mmol, distilled from calcium hydride) of triethylamine in 3 mL of methylene chloride (distilled from phosphorous pentoxide) cooled to 0° was added 122 mg (0.54 mmol, Aldrich) of 2-naphthalenesulfonyl chloride in one portion. The reaction mixture was stirred for 30 minutes then partitioned between 25 mL of ethyl acetate and 25 mL of water. The organic layer was separated, washed with 25 mL of brine, dried (sodium sulfate) and concentrated in vacuo to give an oil. The crude material was purified by flash chromatography (Merck silica, 12×3.0 cm, 2:98 methanol/ethyl acetate) to give an oil which was crystallized (ethyl acetate/hexane) to afford 230 mg (0.47 mmol, 87%) of (S)-N-[4-[(1H-imidazol-2-yl)thio]-1-[(4-methyl-1-piperidinyl)carbonyl] butyl]-2-naphthalenesulfonamide as a solid white foam.

Analysis calcd for $C_{24}H_{30}N_4O_3S_2 \cdot 0.33H_2O$:
C, 58.53; H, 6.27; N, 11.37; S, 13.02.
Found. C, 58.70; H, 6.26; N, 11.20; S, 12.85.

EXAMPLE 4

(S)-5-(Dimethylamino)-N-[4-[(1H-imidazol-2-yl)-thio]-1-[(4-methyl-1-piperidinyl)carbonyl]butyl]-1-naphthalenesulfonamide To a solution of 100 mg (0.27 mmol) of Example 3, Part B amine hydrochloride and 0.15 mL (1.1 mmol, distilled from calcium hydride) of triethylamine in 2 mL of methylene chloride (distilled from phosphorous pentoxide) cooled to 0° was added 73 mg (0.27 mmol, Aldrich) of dansyl chloride in one portion. The reaction mixture was stirred for 30 minutes then partitioned between 20 mL of ethyl acetate and 20 mL of water. The organic layer was separated, dried (sodium sulfate) and concentrated in vacuo to give a yellow-green oil. The crude material was purified by flash chromatography (Merck silica, 12×5.0 cm, 2:98 methanol/ethyl acetate) to afford 134 mg (0.25 mmol, 94%)of (S)-5-(dimethylamino)-N-[4-[(1H-imidazol-2-yl)thio]-1-[(4-methyl-1-piperidinyl)carbonyl]butyl]-1-naphthalenesulfonamide as a pale green solid foam.

Analysis calcd for $C_{26}H_{35}N_5O_3S_2$:
C, 58.95; H, 6.66; N, 13.22; S, 12.10.
Found: C, 58.62; H, 6.56; N, 12.85; S, 12.09.

EXAMPLE 5

(S)-N-[4-[(1H-Imidazol-2-yl)thio]-1-[(4-methyl-1-piperidinyl)carbonyl]butyl]-7-methoxy-2-naphthalenesulfonamide A. 7-Methoxy-2-naphthalenesulfonamide acid, sodium salt To a slurry of 10.0 g (40.6 mmol) of 2-naphthol-7-sulfonic acid (TCI America) in 60 mL of 2:1 water/ethanol was added 1.79 g (44.7 mmol) of sodium hydroxide pellets at room temperature. The mixture was stirred until homogeneous then added in one portion was 5.63 g (44.7 mmol, Aldrich) of dimethylsulfate. A precipitate formed after 15 minutes. The reaction mixture was stirred for 18 hours then concentrated in vacuo. The solid residue was slurried with ~150 mL of absolute ethanol then filtered. The solid was collected on a Buchner funnel and dried to give 10.5 g of crude product. The crude material was slurried with 100 mL of 95% ethanol, heated to reflux then allowed to cool to room temperature. The resulting mixture was filtered on a Buchner funnel. The solid was collected and dried in vacuo to afford 9.16 g (35.2 mmol, 87%) of title compound as a pale brown solid.

B. 7-Methoxy-2-naphthalenesulfonyl chloride

To a mixture of 3.00 g (11.5 mmol) of Part A compound and 4.8 mL (52 mmol) of phosphorous oxychloride was added 3.00 g (14.4 mmol, Aldrich) of phosphorous pentachloride at room temperature. The mixture was warmed gently until homogeneous (bubbling) then heated to reflux (bath temperature 125°) for 4 hours. The resulting dark reaction mixture was cooled in an ice-bath, added slowly to 30 g of ice-water then extracted with 50 mL of chloroform. The chloroform extract was washed with 25 mL of water, 25 mL of saturated aqueous sodium bicarbonate solution, dried (magnesium sulfate) and concentrated in vacuo to give an oil. The crude material was purified by flash chromatography (Merck silica, 12×3.0 cm, methylene chloride) to afford 1.58 g (6.16 mmol, 54%) of title compound as a pale brown solid.

C. (S)-N-[4-[(1H-Imidazol-2-yl)thio]-1-[(4-methyl-1-piperidinyl)carbonyl]butyl]-7-methoxy-2-naphthalenesulfonamide To a solution of 100 mg (0.27 mmol) of Example 3, Part B amine hydrochloride and 0.15 mL (1.1 mmol, distilled from calcium hydride) of triethylamine in 2 mL of methylene chloride (distilled from phosphorous pentoxide) cooled to 0° was added 69 mg (0.27 mmol) of Part B sulfonyl chloride in one portion. The reaction mixture was stirred for 30 minutes then partitioned between 20 mL of ethyl acetate and 20 mL of water. The organic layer was separated, dried (sodium sulfate) and concentrated in vacuo to give an oil. The crude material was purified by flash chromatography (Merck silica, 12×5.0 cm, 4:96 methanol/ethyl acetate) to afford 123 mg (0.24 mmol, 88%) of title compound as a white solid foam.

Analysis Calcd for $C_{25}H_{32}N_4O_4S_2$:
C, 58.12; H, 6.24; N, 10.84; S, 12.41.
Found: C, 57.87; H, 6.27; N, 10.51; S, 12.18.

EXAMPLE 6

(S)-N-[4-[(1H-Imidazol-2-yl)thio]-1-[(4-methyl-1-piperidinyl)carbonyl]butyl]-3-methyl-8-quinolinesulfonamide

A. 3-Methyl-8-quinolinesulfonyl chloride

To 9.0 mL (135 mmol, Fisher) of chlorosulfonic acid was added dropwise with stirring at room temperature 5.00 g (35.0 mmol, Lancaster) of 3-methyl-quinoline over ~5 minutes. The addition was exothermic. The resulting dark solution was heated to 140°–145°, stirring for 5 h, then cooled to 125°. To the cooled reaction mixture was added dropwise over 15 rain 3.3 mL (45 mmol, Mallinckrodt) of thionyl chloride, and the reaction mixture was then heated to 1400 for 1 h. The reaction mixture was cooled to room temperature, then cooled in an ice-bath and added slowly to 50 g of ice. Chloroform (50 mL) was added to the resulting slurry and stirred until the ice melted to give two layers. The aqueous layer was separated and extracted with 30 mL of chloroform. The chloroform layers were combined, washed with two-50 mL portions of 5% aqueous sodium bicarbonate solution, 50 mL of water, dried (sodium sulfate) and concentrated in vacuo to give 4.6 g of a crude light brown solid. The crude material was recrystallized (~20 mL toluene), and the crystals were washed with hexane and dried in vacuo to afford 2.89 g (12.0 mmol, 34%) of title compound as small pale brown crystals, mp 158°–159°.

B. (S)-N-[4-[(1H-Imidazol-2-yl)thio]-1-[(4-methyl-1-piperidinyl)carbonyl]butyl]3-methyl-8-quinolinesulfonamide To a solution of 120 mg (0.33 mmol) of Example 3 Part B amine hydrochloride and 185 μL (1.3 mmol, distilled from calcium hydride) of triethylamine in 2 mL of methylene chloride (distilled from phosphorous pentoxide) cooled to 0°, was added 75 mg (0.31 mmol) of Part A sulfonyl chloride in one portion. The reaction mixture was stirred for 15 minutes then partitioned between 20 mL of ethyl acetate and 20 mL of water. The organic layer was separated, dried (sodium sulfate) and concentrated in vacuo to give an oil. The crude material was purified by flash chromatography (Merck silica, 12×1.5.0 cm, 1:4:16 methanol/methylene chloride/ethyl acetate) to afford 126 mg (0.25 mmol, 81%) of title compound as a white solid foam.

Analysis calcd for $C_{24}H_{31}N_5O_3S_2$:
C, 57.46; H, 6.23; N, 13.96; S, 12.78
Found: C, 57.45; H, 6.33; N, 13.71; S, 12.91.

EXAMPLE 7

(S)-1,2,3,4-Tetrahydro-N-[4-[(1H-imidazol-2-yl)thio]-1-[(4-methyl-1-piperidinyl)carbonyl]butyl]-3-methyl-8-quinolinesulfonamide

A. (S)-γ-[[(1,1-Dimethylethoxy)carbonyl]amino]-4-methyl-δ-oxo-1-piperidinepentanoic acid, phenylmethyl ester To a stirred mixture of N-Boc-L-glutamic acid-γ-benzyl ester (3.00 g, 8.90 mmol) and 1-hydroxybenzotriazole monohydrate (1.50 g, 8.90 mmol) in 40 mL of DMF under argon was added in order:N-methylmorpholine (1.96 mL, 17.8 mmol), 4-methylpiperidine (1.05 mL, 8.90 mmol) and ethyl 3-(3-dimethylamino)propyl carbodiimide hydrochloride (1.71 g, 8.90 mmol). The mixture was stirred at room temperature for 15 h and concentrated in vacuo. The resulting crude oil was dissolved in 300 mL of EtOAc and washed with 0.2N aqueous NaOH (2×60 mL), 1N aqueous HCl (2×60 mL), saturated NaHCO₃ solution (1×60 mL) and brine (1×60 mL). The EtOAc layer was dried over MgSO₄, filtered and concentrated in vacuo to give title amide (3.63 g, 98%).

B. (S)-γ-Amino-4-methyl-δ-oxo-1-piperidinepentanoic acid, phenylmethyl ester To a stirred mixture of Part A amide (3.43 g, 8.21 mmol) in 20 mL of dry dichloromethane under argon at 0° C. was added 40 mL of trifluoroacetic acid (TFA). The mixture was stirred at 0° C. for 1.5 h and at room temperature for 2 h. The mixture was diluted with 100 mL of toluene and concentrated in vacuo. The residue was treated with 30 mL of 4N HCl in ether, diluted with 100 mL of toluene and concentrated in vacuo to give title amine hydrochloride in a quantitative yield.

C.
(S)-4-Methyl-γ-[[(3-methyl-8-quinolinyl)sulfonyl]amino]-δ-oxo-1-piperidinepentanoic acid, phenylmethyl ester To a solution of 3.00 g (8.47 mmol) of Part B amine salt in 50 mL of methylene chloride (distilled from phosphorous pentoxide) cooled to 0° was added 3.5 mL (25 mmol, distilled from calcium hydride) of triethylamine. To the resulting slurry was added 2.04 g (8.46 mmol) of Example 6 Part A sulfonyl chloride. The reaction mixture was stirred at 0° for 1 hr, then 1 mL of concentrated ammonium hydroxide solution was added and after several minutes the reaction mixture was poured into 50 mL of water. The organic layer was separated, dried (sodium sulfate) and concentrated in vacuo to give an oil. The crude material was purified by flash chromatography (Merck silica, 14×5.0 cm, 2:1 ethyl acetate/hexane) to afford 4.15 g (7.93 mmol, 94%) of title compound as a solid white foam.

D.
(S)-N-[4-Hydroxy-1-[(4-methyl-1-piperidinyl)carbonyl]butyl]-3-methyl-8-quinolinesulfonamide To a solution of 4.10 g (7.84 mmol) of Part C ester in 50 mL of anhydrous ethanol (Aldrich) cooled in an ambient water bath was added 1.33 g (31.3 mmol) of lithium chloride, then after several minutes, 597 mg (15.7 mmol, Aldrich) of sodium borohydride was added. The reaction mixture was stirred for 18 h then a second 597 mg portion of sodium borohydride was added and stirring continued for 8 h. The resulting thick mixture was quenched by slow addition of 60 mL of water then concentrated in vacuo and the residue partitioned between 100 mL of 1N aq NaOH solution and 75 mL of methylene chloride. The aqueous layer was separated and extracted with an additional 75 mL of methylene chloride. The organic extracts were combined, dried (sodium sulfate) and concentrated in vacuo to give a yellow oil. The crude material was purified by flash chromatography (Merck silica, 18×5.0 cm, 1:20 methanol/ethyl acetate) to afford 2.30 g (5.49 mmol, 70%) of title compound as a solid.

E.
(S)-1,2,3,4-Tetrahydro-N-[4-hydroxy-1-[(4-methyl-1-piperidinyl)carbonyl]butyl]-3-methyl-8-quinolinesulfonamide A mixture of 2.00 g (4.77 mmol) of Part D alcohol in 40 mL of absolute ethanol (Aldrich) was warmed until homogeneous then cooled to room temperature. To the resulting solution was added 5.0 mL of 1M aq HCl solution then 1.00 g of 10% palladium on activated carbon catalyst (Aldrich) and the mixture stirred under hydrogen (balloon) for 18 h. The reaction mixture was filtered on a Buchner funnel then passed through a 0.4 μM polycarbonate membrane and neutralized by addition of 500 mg (10 mmol) of solid sodium bicarbonate. The resulting solution was concentrated in vacuo and the residue partitioned between 30 mL of methylene chloride and 30 mL of water. The aqueous layer was separated and extracted with 30 mL of methylene chloride then 30 mL of ethyl acetate. The organic extracts were combined, dried (sodium sulfate) and concentrated in vacuo to afford 1.83 g (4.32 mmol, 91%) of title alcohol as a solid white foam.

F.
(S)-1,2,3,4-Tetrahydro-N-[4-iodo-1-[(4-methyl-1-piperidinyl)carbonyl]butyl]-3-methyl-8-quinolinesulfonamide To a solution of 250 mg (0.59 mmol) of Part E alcohol in 2 mL of methylene chloride (distilled from phosphorous pentoxide) cooled to −20° was added 120 μL (0.86 mmol, distilled from calcium hydride) of triethylamine then dropwise 60 μL (0.78 mmol, Aldrich) of methanesulfonyl chloride. The reaction mixture was stirred for 15 minutes then partitioned between 15 mL of water containing 0.10 mL of 1M aq HCl solution and 15 mL of ethyl acetate. The organic layer was separated, washed with 15 mL of water, 15 mL of brine, dried (sodium sulfate) and concentrated in vacuo to give the crude mesylate as a colorless oil. The crude mesylate (~0.59 mmol) was solubilized in 3 mL of reagent acetone then 440 mg (2.93 mmol, Aldrich) of sodium iodide was added. The reaction mixture was heated to 45° for 2.5 h then cooled to room temperature and partitioned between 20 mL of 5% aq sodium thiosulfate solution and 20 mL of ethyl acetate. The organic layer was separated, washed with 20 mL of saturated aq sodium bicarbonate solution, 20 mL of brine, dried (sodium sulfate) and concentrated in vacuo to give an oil. The crude material was purified by flash chromatography (Merck silica, 12×1.5 cm, 1:2 ethyl acetate/hexane) to afford 220 mg (0.41 mmol, 70%) of title iodide as a white solid.

G.
(S)-1,2,3,4-Tetrahydro-N-[4-[(1H-imidazol-2-yl)-thio]-1-[(4-methyl-1-piperidinyl)carbonyl]butyl]-3-methyl-8-quinolinesulfonamide A mixture of 215 mg (0.40 mmol) of Part F iodide and 120 mg (1.20 mmol, Aldrich) of 2-mercaptoimidazole in 2 mL of sieve-dried DMF was stirred until homogeneous then placed in a 65° oil bath. The reaction mixture was stirred for 15 minutes then cooled to room temperature and partitioned between 20 mL of 1M aq NaOH solution and 20 mL of ethyl acetate. The organic layer was separated, washed with 20 mL of 1M aq NaOH solution, 20 mL of water, 10 mL of brine, dried (sodium sulfate) and concentrated in vacuo to give a colorless oil. The crude material was purified by flash chromatography (Merck silica, 12×1.5 cm, 1:19 methanol/ethyl acetate) to afford 165 mg (0.32 mmol, 82%) of title compound as a solid white foam.

Analysis calcd for $C_{24}H_{35}N_5O_3S_2$:
C, 57.00; H, 6.98; N, 13.85; S, 12.68
Found: C, 57.24; H, 7.04; N, 13.59; S, 12.69.

EXAMPLE 8
(S)-N-[1-[(4-Methyl-1-piperidinyl)carbonyl]-4-(2-pyridinylthio)butyl]-2-naphthalenesulfonamide

A.
(S)-γ-[[(1,1-Dimethylethoxy)carbonyl]amino]-4-methyl-δ-oxo-1-piperidinepentanoic acid, phenylmethyl ester To a clear solution of 8.00 g (23.7 mmol, Bachem) of N-Boc-L-glutamic acid-γ-benzyl ester, in 150 mL of DMF was added 3.1 mL (26 mmol, Aldrich) of 4-methylpiperidine and 4.0 g (26 mmol, Schweizerhall) of 1-hydroxybenzotriazole monohydrate. The mixture was cooled to 0° C. and treated with 5.2 mL (47 mmol, Aldrich) of 2-methylmorpholine, followed by the addition of 5.0 g (26 mmol, Bachem) of WSC. The mixture was stirred at 0° C. for 2 hrs and at room temperature for 4 hrs. The mixture was concentrated in high vacuum. The residue was worked up with 300 mL of EtOAc, washed with 200 mL of 1N HCl and 200 mL of a saturated aqueous solution of NaHCO$_3$, H$_2$O and brine; dried (MgSO$_4$) and concentrated in vacuo to afford 9.92 g (23.7 mmol, 100%) of title compound as a clear oil.

B.

(S)-γ-[Bis[(1,1-dimethylethoxy)carbonyl]amino]-4-methyl-γ-oxo-1-piperidinepentanoic acid, phenylmethyl ester To a syrup of 6.50 g (15.5 mmol) of Part A ester in 1.0 mL of acetonitrile was added 1.38 g (9.3 mmol, Aldrich) of 4-pyrrolidinopyridine and treated with 43.4 g (199 mmol, Fluka) of ditertbutyl dicarbonate dropwise over a period of 6 hrs at 87° C. The resulting black light oil was purified by flash chromatography (280 g, Merck silica gel, 15% EtOAc/hexane) to afford pure 4.7 g (9.0 mmol, 60%) of title ester as a clear oil.

C.

(S)-[4-Hydroxy-1-[(4-methyl-1-piperidinyl)carbonyl]butyl]imidodicarbonic acid, bis(1,1-dimethylethyl) ester A light yellow solution of 4.4 g (8.5 mmol) of Part B ester in 50 mL (Aldrich) anhydrous EtOH was treated with 1.44 g (34 mmol, Aldrich) of lithium chloride. The slurry was allowed to stir at room temperature for 15 min. until the solid was completely dissolved. The yellow solution mixture was treated with 642 mg (17 mmol, Aldrich) of sodium borohydride. The mixture was stirred at room temperature for 26 hrs. The mixture was treated then with a second portion of 1.44 g (34 mmol, Aldrich) of lithium chloride and 642 mg (17 mmol, Aldrich) of sodium borohydride. After being stirred at room temperature 24 hrs, the mixture was treated with a third portion of 1.44 g (34 mmol, Aldrich) of lithium chloride and 642 mg (17 mmol, Aldrich) of sodium borohydride and allowed to stir for 24 hrs. The crude reaction mixture was quenched with 10 mL of H$_2$O. The mixture was concentrated in vacuo. The residue was partitioned between 100 mL of 0.5N HCl and 200 mL of EtOAc. The organic layer was separated and washed with 100 mL of a saturated aqueous solution of NaHCO$_3$ and brine; dried (MgSO$_4$) and concentrated in vacuo. The residue was purified by flash chromatrography (100 g, Merck silica gel, 40% EtOAc/hexane) to afford 2.5 g (6.0 mmol, 71%) of pure title alcohol as a clear oil.

D.

(S)-[1-[(4-Methyl-1-piperidinyl)carbonyl]-4-[(methylsulfonyl)oxy]butyl]imidodicarbonic acid, bis(1,1-dimethylethyl) ester A clear solution of 2.5 g (6.0 mmol) of Part C alcohol in 10 mL of CH$_2$Cl$_2$ (distilled from P$_2$O$_5$) was cooled to −20° C. and treated with 1.3 mL (9.0 mmol) of triethylamine (Et$_3$N) (distilled from CaH$_2$), followed by the addition of 0.60 mL (7.3 mmol, Aldrich) of methanesulfonyl chloride. The mixture was stirred at −20° C. for 1 hr. The crude mixture was diluted with 20 mL of CH$_2$Cl$_2$, washed with 20 mL of 1N HCl and 20 mL of a saturated aqueous solution of NaHCO$_3$ and brine; dried (MgSO$_4$), and concentrated in vacuo to afford 2.9 g(5.9 mmol, 97%) of title mesylate.

E.

(S)-[4-Iodo-1-[(4-methyl-1-piperidinyl)carbonyl]butyl]imidodicarbonic acid, bis(1,-dimethylethyl) ester To the light yellow solution of 2.8 g (5.6 mmol) of Part D mesylate in 60 mL fresh acetone (Burdick and Jackson) was added 4.2 g (28 mmol) of sodium iodide. The mixture was stirred in dark and at room temperature for 16 hrs. The crude reaction mixture was concentrated in vacuo. The residue was diluted with EtOAc, washed with 200 mL aqueous 5% sodium thiosulfate and an aqueous solution of saturated NaHCO$_3$ and brine; dried (MgSO$_4$) and concentrated in vacuo to give 2.73 g (5.20 mmol, 93%) of title iodide.

F.

(S)-[1-[(4-Methyl-1-piperidinyl)carbonyl]-4-(2-pyridinylthio)butyl]imidodicarbonic acid, bis(1,1-dimethylethyl) ester To a solution of 80 mg (0.72 mmol, Aldrich) of 2-mercaptopyridine, in 1 mL of sieve-dried DMF cooled to 0° was added 29 mg (60% in oil, 0.72 mmol, Aldrich) of sodium hydride dispersion, gas evolution. The mixture was stirred for 15 minutes then to the resulting yellow anion solution was added dropwise a solution of 400 mg (0.76 mmol) of Part E iodide in 2 mL of DMF. The reaction mixture was stirred for 15 minutes then partitioned between 20 mL of ethyl acetate and 20 mL of water. The organic layer was separated, washed with 20 mL of water, dried (sodium sulfate) and concentrated in vacuo to give a yellow oil. The crude material was purified by flash chromatography (Merck silica, 12×3.0 cm, 1:3 ethyl acetate/hexane) and afforded 343 mg (0.68 mmol, 94%) of title compound as a colorless oil.

G.

(S)-2-Amino-1-(4-methyl-1-piperidinyl)-5-(2-pyridinylthio)-1-pentanone, dihydrochloride To a solution of 340 mg (0.67 mmol) of Part F compound in 0.5 mL of dioxane (Burdick and Jackson) cooled in an ambient water bath was added 2.0 mL (4M in dioxane, 8.0 mmol, Aldrich) of hydrogen chloride solution. The solution was stirred for 20 hr then concentrated in vacuo. The residue was solubilized with 5 mL of methanol then concentrated in vacuo, repeated two additional times to afford 253 mg (0.67 mmol, 100%) of title amine salt as a pale yellow solid foam.

H.

(S)-N-[1-[(4-Methyl-1-piperidinyl)carbonyl]-4-(2-pyridinylthio)butyl]-2-naphthalenesulfonamide To a solution of 80 mg (0.21 mmol) of Part G amine hydrochloride in 2 mL of methylene chloride (distilled from phosphorous pentoxide) cooled to 0° was added 120 μL (0.85 mmol, distilled from calcium hydride) of triethylamine then 47 mg (0.21 mmol, Aldrich) of 2-napthalenesulfonyl chloride in one portion. The reaction mixture was stirred for 30 minutes then partitioned between 20 mL of ethyl acetate and 20 mL of water. The organic layer was separated, washed with 20 mL of brine, dried (sodium sulfate) and concentrated in vacuo to give a solid. The crude material was purified by flash chromatography (Merck silica, 12×1.5.0 cm, 1:1 ethyl acetate/hexane) followed by recrystallization (ethyl acetate/hexane) to afford 80 mg (0.16 mmol, 77%) of title compound as a white solid, mp 131°-132°.

Analysis calcd for C$_{26}$H$_{31}$N$_3$O$_3$S$_2$.

C, 62.75; H, 6.28; N, 8.44; S, 12.88

Found: C, 63.05; H, 6.31; N, 8.59; S, 12.88.

EXAMPLE 9

(S)-N-[1-[(4-Methyl-1-piperidinyl)carbonyl]-5-(2-pyridinyl)pentyl]-2-naphthalenesulfonamide

A.
2-[(Trimethylsilyl)methyl]pyridine

Prepared as described by Musker, W. K.; Scholl, R. L. *J. Organometal. Chem.*, 1971, 27, 37–43.

To a solution of 55 mL (1.8M in ether/cyclohexane, 99 mMol, Aldrich) of phenyllithium solution at room temperature was added dropwise over ~5 minutes 9.30 g (100 mmol, Aldrich) of 2-picoline. The addition was mildly exothermic, cooling was unnecessary. The reaction mixture was stirred for 1 h then 6.3 mL (50 mmol, Petrarch) of chlorotrimethylsilane was added dropwise over ~10 minutes. The addition was mildly exothermic. The reaction mixture was stirred for 16 h, quenched by slow addition of 5 mL of water then partitioned between 50 mL of water and 25 mL of ether. The organic layer was separated, washed with two-50 mL portions of water, 25 mL of brine, dried (sodium sulfate) and concentrated in vacuo to give an orange liquid. The crude material was purified by flash chromatography (Merck silica, 22×5.0 cm, hexane then 1:9 ethyl acetate/hexane) followed by distillation (bulb-to-bulb, 10 mm, 25°–100°) to afford 6.20 g (37.6 mmol, 75%) of title silane as a clear, colorless liquid.

B.
(S)-[1-[(4-Methyl-1-piperidinyl)carbonyl]-4-oxobutyl]imidodicarbonic acid, bis(1,1-dimethylethyl) ester To a solution of 3.5 mL (2.0M in methylene chloride, 7.0 mmol, Aldrich) of oxalyl chloride solution in 5 mL of methylene chloride (distilled from phosphorous pentoxide) cooled to −78° was added dropwise a solution of 0.90 mL (13 mmol, Burdick and Jackson) of dimethylsulfoxide in 3 mL of methylene chloride over several minutes. The reaction mixture was stirred for 15 minutes then a solution of 1.00 g (2.42 mmol) of Example 8 Part C alcohol in 5 mL of methylene chloride was added. The reaction mixture was stirred for an additional 30 minutes then 2.6 mL (18 mmol, distilled from calcium hydride) of triethylamine was added dropwise. The resulting solution was warmed to 0° after 5 minutes, stirred for 10 minutes then partitioned between 15 mL of methylene chloride and 20 mL of water. The organic layer was separated, dried (magnesium sulfate) and concentrated in vacuo to give an oil. The crude material was purified by flash chromatography (Merck silica, 15×3.0 cm, 1:1 ethyl acetate/hexane) to afford 847 mg (2.06 mmol, 85%) of title aldehyde as a pale yellow oil.

C.
S)-[1-[(4-Methyl-1-piperidinyl)carbonyl]-5-(2-pyridinyl)-4-pentenyl]imidodicarbonic acid, bis(1.1-dimethylethyl) ester To a solution of 0.30 mL (2.2 mmol, distilled from calcium hydride) of diisopropylamine in 3 mL of THF (distilled from sodium/benzophenone) cooled to −78° was added dropwise 0.65 mL (2.5M in hexane, 1.6 mmol, Aldrich) of n-butyllithium solution. The solution was stirred for 15 minutes then 300 mg (1.82 mmol) of Part A silane was added dropwise. The reaction mixture was stirred for 15 minutes to give an orange-yellow solution of the anion. The anion solution was added rapidly via cannula to a stirred solution of 590 mg (1.43 mmol) of Part B aldehyde in 4 mL of THF cooled to −78°. The reaction mixture was stirred for 5 minutes at −78° then warmed to 0° and after 15 minutes quenched by the addition of 1 mL of water. The mixture was added to 30 mL of water and extracted with two-20 mL portions of ethyl acetate. The organic extracts were combined, washed with 25 mL of brine, dried (sodium sulfate) and concentrated in vacuo to give a yellow oil. The crude material was partially purified by flash chromatography (Merck silica, 15×3.0 cm, 1:2 ethyl acetate/hexane) to afford title compound contaminated with starting Part B aldehyde.

To a solution of impure Part B aldehyde in 3 of methanol cooled to 0° was added 30 mg (0.79 mmol, Aldrich) of sodium borohydride. The reaction mixture was stirred for 15 minutes then quenched by addition of several drops of water followed by concentration in vacuo. The residue was partitioned between 15 mL of ethyl acetate and 15 mL of 1M aq NaOH solution. The aqueous layer was separated and extracted with an additional 15 mL of ethyl acetate. The organic extracts were combined, dried (sodium sulfate) and concentrated in vacuo to give an oil. The crude material was purified by flash chromatography (Merck silica, 15×3.0 cm, 1:1 ethyl acetate/hexane) to afford 450 mg (0.92 mmol, 65%) of title compound as a colorless oil.

D.
(S)-[1-[(4-Methyl-1-piperidinyl)carbonyl]-5-(2-pyridinyl)-4-pentyl]imidodicarbonic acid, bis(1,1-dimethylethyl) ester A mixture of 445 mg (0.91 mmol) of Part C compound and 45 mg of 10% palladium on activated carbon calalyst (Aldrich) in 5 mL of methanol (Burdick and Jackson) was stirred under an atmosphere of hydrogen (balloon) for 16 h. The reaction mixture was passed through a 0.4μM polycarbonate membrane to separate the catalyst then the filtrate was concentrated in vacuo to give an oil. The crude material was purified by flash chromatography (Merck silica, 15×3.0 cm, 2:1 ethyl acetate/hexane) to afford 305 mg (0.62 mmol, 69%) of title compound as a colorless oil.

E.
(S)-2-Amino-1-(4-methyl-1-piperidinyl)-6-(2-pyridinyl)-1-hexanone, dihydrochloride To a solution of 300 mg (0.61 mmol) of Part D compound in 0.5 mL of dioxane (Burdick and Jackson) was added at room temperature 2.0 mL (4M in dioxane, 8.0 mmol, Aldrich) of hydrogen chloride solution. The reaction mixture was stirred for 3 h then concentrated in vacuo to give an oil. The oil was solubilized with 5 mL of methanol and concentrated in vacuo; repeated two additional times to afford 222 mg (0.61 mmol, 100%) of title amine hydrochloride as a solid white foam.

F.
(S)-N-[1-[(4-Methyl-1-piperidinyl)carbonyl]-5-(2-pyridinyl)pentyl]-2-naphthalenesulfonamide To a solution of 40 mg (0.11 mmol) of Part E amine hydrochloride in 2 mL of methylene chloride (distilled from phosphorous pentoxide) cooled to 0° was added 65 μL (0.46 mmol, distilled from calcium hydride) of triethylamine then 25 mg (0.11 mmol, Aldrich) of 2-napthalenesulfonyl chloride in one portion was added. The reaction mixture was stirred for 30 minutes then partitioned between 20 mL of ethyl acetate and 20 mL of water. The organic layer was separated, washed with 20 mL of brine, dried (magnesium sulfate) and concentrated in vacuo to give an oil. The crude material was purified by flash chromatography (Merck silica, 15×1.5.0 cm, ethyl acetate) to afford 45 mg (0.094 mmol, 85%) of title compound as a solid white foam.

Analysis calcd for $C_{27}H_{33}N_3O_3S$:
C, 67.61; H, 6.93; N, 8.76; S, 6.68
Found: C, 67.49; H, 6.92; N, 8.94; S, 7.07.

EXAMPLE 10

(S)-7-Methoxy-N-[1-[(4-methyl-1-piperidinyl)carbonyl]-5-(2-pyridinyl)pentyl]-2-naphthalenesulfonamide To a solution of 80 mg (0.22 mmol) of Example 9 Part E amine hydrochloride in 2 mL of methylene chloride (distilled from phosphorous pentoxide) cooled to 0° was added 125 μL (0.89 mmol, distilled from calcium hydride) of triethylamine, then 56 mg (0.22 mmol) of Example 5 Part B sulfonyl chloride was added in one portion. The reaction mixture was stirred for 30 minutes, then partitioned between 20 mL of ethyl acetate and 20 mL of water. The organic layer was separated and the aqueous layer extracted with an additional 10 mL of ethyl acetate. The combined oraganic layers were washed with 20 mL of brine, dried (magnesium sulfate) and concentrated in vacuo to give an oil. The crude material was purified by flash chromatography (Merck silica, 15×1.5.0 cm, ethyl acetate) to afford 87 mg (0.17 mmol, 78%) of title compound as a solid white foam.

Analysis calcd for $C_{28}H_{35}N_3O_4S$:
C, 65.99; H, 6.92; N, 8.24; S, 6.29
Found: C, 65.65; H, 6.87; N, 8.75; S, 6.43.

Other compounds of the invention which may be prepared following the procedures set out in the specification and working Examples are set out below.

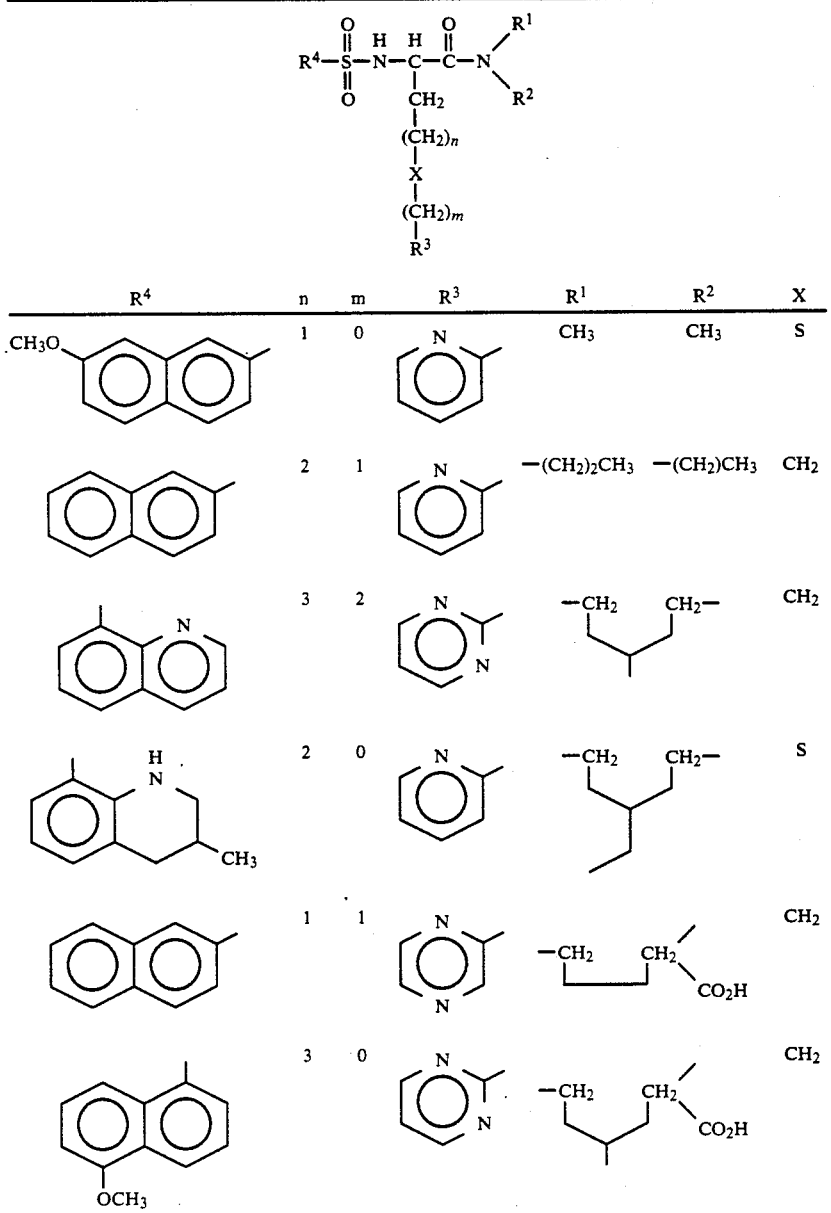

-continued

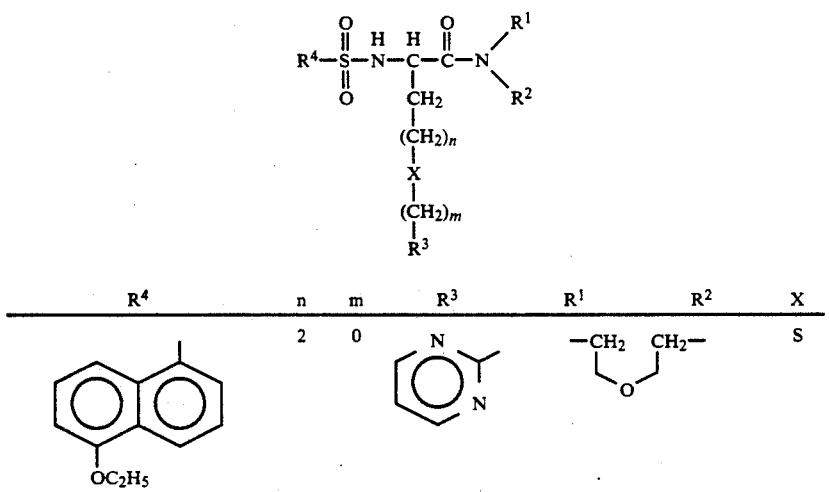

What is claimed is:

1. A compound of the structure

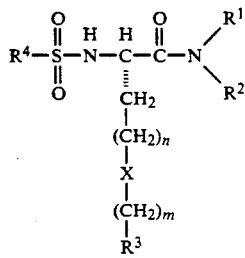

including all stereoisomers thereof,
wherein
X is —S—;
m is 0, 1 or 2;
n is 1, 2 or 3;
$R^1$ and $R^2$ may be the same or different and are independently hydrogen, lower alkyl, cycloalkyl, aryl, heteroaryl, or heteroarylalkyl, or $R^1$ and $R^2$ can be taken together with the nitrogen atom to which they are attached to form a 5- to 8-membered N-containing heterocyclic ring, which may optionally contain an additional N, O or S atom in the ring, which may be unsubstituted or substituted on the N-atom or a carbon atom with lower alkyl, carboxy, amido, carboalkoxy, aryl, cycloalkyl, hydroxy, alkoxy, amino, alkylamino or dialkylamino;
$R^3$ is heteroaryl;
$R^4$ is aryl, quinolinyl, or tetrahydroquinolinyl; wherein the term "heteroaryl" by itself or as part of another group refers to a 5- or 6-membered monocyclic aromatic ring which includes 1 or 2 hetero atoms which are nitrogen, oxygen or sulfur any of which may optionally include 1 or 2 substituents which is halogen, lower alkyl, lower alkoxy, cyano, hydroxy, carboxy, amido, carboalkoxy, aryl, cycloalkyl, alkylthio, alkylsulfinyl, alkylsulfonyl, arylthio, arylsulfinyl, arylsulfonyl, amino, lower alkylamino and/or di-lower alkylamino; and pharmaceutically acceptable salts thereof.

2. The compound as defined in claim 1 wherein $R^3$ is heteroaryl.

3. The compound as defined in claim 1 wherein $R^3$ is imidazolyl.

4. The compound as defined in claim 1 wherein $R^3$ is

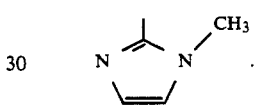

5. The compound as defined in claim 1 wherein $R^3$ is pyridyl.

6. The compound as defined in claim 1 wherein $R^4$ is aryl.

7. The compound as defined in claim 1 wherein $R^4$ is 2-naphthyl.

8. The compound as defined in claim 1 wherein $R^4$ is

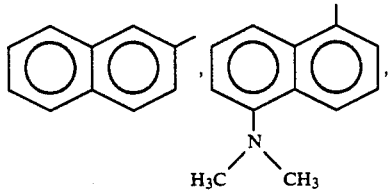

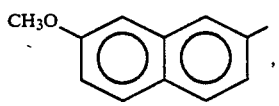

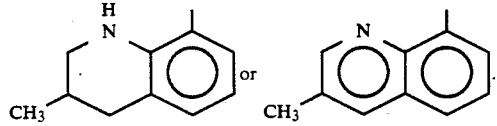

9. The compound as defined in claim 1 wherein $R^1$ and $R^2$ are taken together with the N-atom to which they are attached to form a 5- to 8-membered heterocyclic.

10. The compound as defined in claim 9 wherein $R^1$ and $R^2$ are taken together with the N-atom to which they are attached to form

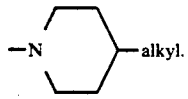

11. The compound as defined in claim 10 wherein alkyl is CH₃.

12. The compound as defined in claim 1 wherein n is 2 and m is 0.

13. The compound as defined in claim 1 which is (S)-N-[4-[(1-methyl-1H-imidazol-2-yl)thio]-1-[(4-methyl-1-piperidinyl)carbonyl]butyl]-2-naphthalenesulfonamide;

(S)-5-(dimethylamino)-N-[4-[(1-methyl-1H-imidazol-2-yl)thio]-1-[(4-methyl-1-piperidinyl)carbonyl]-butyl]-1-naphthalenesulfonamide;

(S)-N-[4-[(1-imidazol-2-yl)thio]-1-[(4-methyl-1-piperidinyl)carbonyl]butyl]-2-naphthalenesulfonamide;

(S)-5-(dimethylamino)-N-[4-[(1H-imidazol-2-yl)thio]-1-[(4-methyl-1-piperidinyl)carbonyl]-butyl]-1-naphthalenesulfonamide;

(S)-N-[4-[(1H-imidazol-2-yl)thio]-1-[(4-methyl-1-piperidinyl)carbonyl]butyl]-7-methoxy-2-naphthalenesulfonamide;

(S)-N-[4-[(1H-imidazol-2-yl)thio]-1-[(4-methyl-1-piperidinyl)carbonyl]butyl]-3-methyl-8-quinolinesulfonamide;

(S)-1,2,3,4-tetrahydro-N-[4-[(1H-imidazol-2-yl)thio]-1-[(4-methyl-1-piperidinyl)carbonyl]butyl]-3-methyl-8quinolinesulfonamide;

(S)-N-[1-[(4-methyl-1-piperidinyl)carbonyl]-4-(2-pyridinylthio)butyl]-2-naphthalenesulfonamide;

or pharmaceutically acceptable salts of any of the above.

14. A method of inhibiting or preventing formation of blood clots, which comprises administering to a patient in need of treatment a therapeutically effective amount of a compound as defined in claim 1.

15. A pharmaceutical composition comprising a compound as defined in claim 1 and a pharmaceutically acceptable carrier thereof.

* * * * *